(12) United States Patent
Schröer et al.

(10) Patent No.: US 11,974,719 B2
(45) Date of Patent: May 7, 2024

(54) METHOD FOR ADAPTIVE FUNCTIONAL RECONFIGURATION OF OPERATING ELEMENTS OF AN IMAGE ACQUISITION SYSTEM AND CORRESPONDING IMAGE ACQUISITION SYSTEM

(71) Applicant: SCHÖLLY FIBEROPTIC GMBH, Denzlingen (DE)

(72) Inventors: Stefan Schröer, Freiburg (DE); Matthias Kühn, Freiburg (DE); Alexander Köhler, Freiburg (DE); Daniel Härter, Emmendingen (DE); Joachim Jauss, Rheinhausen (DE)

(73) Assignee: SCHÖLLY FIBEROPTIC GMBH, Denzlingen (DE)

( * ) Notice: Subject to any disclaimer, the term of this patent is extended or adjusted under 35 U.S.C. 154(b) by 593 days.

(21) Appl. No.: 16/925,624

(22) Filed: Jul. 10, 2020

(65) Prior Publication Data

US 2021/0007588 A1 Jan. 14, 2021

(30) Foreign Application Priority Data

Jul. 10, 2019 (DE) .......................... 102019118752.4

(51) Int. Cl.
*A61B 1/00* (2006.01)
*A61B 1/05* (2006.01)
(Continued)

(52) U.S. Cl.
CPC ...... *A61B 1/0005* (2013.01); *A61B 1/000096* (2022.02); *A61B 1/00042* (2022.02);
(Continued)

(58) Field of Classification Search
CPC ............ A61B 1/0005; A61B 1/000096; A61B 1/00042; A61B 1/05; A61B 1/015;
(Continued)

(56) References Cited

U.S. PATENT DOCUMENTS

2015/0334292 A1 11/2015 Tartz et al.
2016/0337596 A1* 11/2016 Miura ................ H04N 5/23245
(Continued)

FOREIGN PATENT DOCUMENTS

JP 2017127443 A * 7/2017
WO 2016168838 A2 10/2016
(Continued)

OTHER PUBLICATIONS

Dayou Jiang & Jongweon Kim, A Scene Change Detection Framework Based on Deep Learning and Image Matching, 2019, pp. 623-629.

*Primary Examiner* — Timothy J Henn
(74) *Attorney, Agent, or Firm* — Grogan, Tuccillo & Vanderleeden LLP (57) ABSTRACT

In summary, to simplify operation of a medical image acquisition system, it is proposed that the image acquisition system continuously monitors a current image acquisition situation and assigns at least one new function to at least one, preferably manual, operating element, which is adapted to a detected new image acquisition situation, in response to a change in the image acquisition situation, to the extent that said newly assigned function is adjustable and/or operable with the at least one operating element. To this end, the image acquisition system can detect the change in the image acquisition situation using predefined parameters by means of sensors and/or through communication with peripheral units and/or preferably through image analysis of an image sequence which is recorded with an image sensor of the image acquisition system.

23 Claims, 2 Drawing Sheets

(51) Int. Cl.
*G06F 3/01* (2006.01)
*G06T 7/70* (2017.01)
*G06V 10/98* (2022.01)
*H04N 23/611* (2023.01)

(52) U.S. Cl.
CPC ............... *A61B 1/05* (2013.01); *G06F 3/016* (2013.01); *G06T 7/70* (2017.01); *G06V 10/987* (2022.01); *H04N 23/611* (2023.01)

(58) Field of Classification Search
CPC ....... G06F 3/016; G06T 7/70; H04N 5/23219; H04N 5/23216; H04N 5/23293; G06V 10/987
See application file for complete search history.

(56) References Cited

U.S. PATENT DOCUMENTS

2019/0159656 A1* 5/2019 Hale ..................... G06F 3/038
2021/0153730 A1* 5/2021 Karino ................. A61B 1/0005

FOREIGN PATENT DOCUMENTS

WO      2018017625  A1    1/2018
WO   WO-2020137398 A1 *  7/2020   ....... H04N 5/232127

\* cited by examiner

METHOD FOR ADAPTIVE FUNCTIONAL RECONFIGURATION OF OPERATING ELEMENTS OF AN IMAGE ACQUISITION SYSTEM AND CORRESPONDING IMAGE ACQUISITION SYSTEM

CROSS-REFERENCE TO RELATED APPLICATIONS

This application claims the priority benefit of German Patent Application No. 102019118752.4 filed on Jul. 10, 2019, hereby incorporated by reference for all that is disclosed as though fully set forth herein.

FIELD OF THE INVENTION

The invention relates to an image acquisition method, in which an image sequence, particularly in the form of a video image data stream, is recorded with an image sensor of a medical image acquisition system and wherein functions of components of the image acquisition system are set or operated with the assistance of operating elements.

BACKGROUND OF THE INVENTION

In this case, the image sequence may be, for example, a sequence of individual images, which may particularly be present in the form of a video image data stream. Such an image acquisition system may be, for example, an endoscopy system. Said system may comprise an endoscope as one component having an image sensor, particularly in the form of a video endoscope. However, an image acquisition system as previously described may also be designed, for example, as an exoscope or a digital microscope, each with a corresponding image sensor.

The functions which are adjustable and/or operable with the operating elements may accordingly be, for example, functions of such an endoscope/exoscope/digital microscope or, however, a corresponding camera control unit.

The invention further relates to a corresponding medical image acquisition system with an image sensor as well as several control elements for controlling the image acquisition system. Such an image acquisition system in this case may particularly be designed as an endoscopy system and thus comprise an endoscope with an image sensor; however, said system may also be present, for example, in the form of an exoscope or a digital microscope.

Users of such image acquisition systems, particularly such endoscopy systems, are often not capable of fully utilizing the technical options of the systems. A commonplace reason for this is often that the operation, particularly the adjustment of necessary image acquisition parameters, is complicated and tedious. With previously known endoscopy systems, the reason for this is that specifically the operation of the camera head, which reads out and controls the image sensor of the endoscope, and/or of the entire video endoscope is often hardly intuitive and frequently very complex, particularly when the endoscopy system is overloaded with functions.

Thus, the object of the invention is to increase the operability of medical image acquisition systems generally and of endoscopy systems particularly so that the complete functional scope can actually be utilized, specifically in the medical application situation, for example, of surgeons.

This object is achieved according to the invention with an image acquisition method having the features of claim 1. In particular, thus in order to achieve the object according to the invention with an image acquisition method of the aforementioned type, it is proposed that at least one function is reassigned to at least one of the operating elements in response to a detected change in an image acquisition situation.

If the image acquisition system is designed, for example, as an endoscopy system, the endoscopy system, that is generally the medical image acquisition system, can carry out the reassignment automatically, i.e. particularly autonomously.

This automated reassignment and/or reconfiguration of at least one of the operating elements with at least one new function assigns thus at least one function to the at least one operating element, said function not previously being controllable with the at least one operating element before the assignment.

In doing so, the new at least one function can also be assigned to several of the operating elements to the extent that the new function can be operated by several operating elements.

If several of the operating elements are assigned with a new function due to the reconfiguration, several different functions can also simultaneously be distributed to several operating elements. With such an embodiment, thus several functions are reassigned by means of the reconfiguration. With this variant as well, one of these functions can, in turn, be assigned to several of the operating elements.

SUMMARY OF THE INVENTION

It is understood that diverse variations of reassignments and/or reconfigurations of the operating elements are thereby possible. In this case, it may also be provided that it is considered whether the user is left-handed or right-handed. After a one-time user input, the image acquisition system, particularly said endoscopy system, can adapt itself accordingly and carry out the reassignment of the operating elements to be adapted for a left-handed person or a right-handed person.

Furthermore, particular preferences of users with respect to the functional reassignment to be carried out depending on the detected image acquisition situation can also be considered by means of corresponding user inputs. It may also be provided with the reassignment that a previously implemented user input is considered, particularly such that the reassignment corresponds to an individual preference of the user of the image acquisition system.

A change in the image acquisition situation in terms of the invention may particularly be present when an image processing unit of the image acquisition system, particularly of the endoscopy system, detects a specific image acquisition situation. Thus, as an alternative or supplement, it may be provided that the operating elements are reconfigured with functions in response to a detected specific image acquisition situation.

Such specific image acquisition situations may be predefined according to the invention, for example, by means of setting parameters. Accordingly, a particular catalog of predefined image acquisition situations, for example in the form of predefined parameter sets, may also be retained by the image acquisition system/the endoscopy system in order to enable the detection of said predefined image acquisition situations.

Consequently, the basic idea of the invention is to provide only those functions which are respectively suitable, because they are required in the specific situation, from a very extensive total functional scope of the image acquisition system depending on the situation, for example, in order to set parameters.

In other words, the image acquisition system thus reduces the work of the user in that it offers the user a situation-adapted selection with functions adjustable using control elements based on the intelligence of the system. These functions currently adjustable with the operating elements in this case typically only amount to a part of a totality of adjustment options and/or functions of the image acquisition system and any other external devices controllable or adjustable with the operating elements.

This time-adjustable selection of functions adjustable with the operating elements can thus particularly change, particularly reduce, a currently adjustable functional scope as a function of a detected image acquisition situation, namely by means of said reconfiguration, which leads to a reduction of work for the user. The reduction in the functional scope in this case can be seen if one compares the respective functional scope currently adjustable with the operating elements to the complete functional scope of the image acquisition system, which can only be utilized after reassignment of the operating elements with functions which were not adjustable with the operating elements before the reconfiguration.

A reconfiguration of the operating elements with functions makes sense, for example, when a new image acquisition situation requires a respective adaptation of a view/an image/a processing of the image sequence and/or when additional functionality is required which had not been required in a previous image acquisition situation and thus was also not offered.

The image sequence can essentially consist of individual images. However, the image sequence can also be recorded in the form of a video image data stream of the image acquisition system, particularly of an endoscope. This case then involves accordingly a video image acquisition system and/or a video endoscopy system.

As known in the prior art, the operating elements may be designed, for example, as keys, buttons, slide controls, or as rotary controls. They may also be formed, however, by touch-sensitive surfaces, for example as virtual keys on a touch-sensitive display.

Advantages of the method according to the invention are particularly as follows:

the user can easily and quickly access required commands because they are offered to the user by the image acquisition system depending on the situation;

complex searching in submenus can thus be dispensed with;

also a complex understanding of the interactions between individual setting functions is no longer necessary because the image acquisition system detects and considers them;

the user no longer has the burden of complex operation and searching for suitable setting options and can thus concentrate on the actual work at hand with the image acquisition system;

the distraction due to complex operation is minimized which also contributes to patient safety;

the complete functional scope can be utilized simultaneously and thus a better performance can be achieved;

the technical possibilities of the image acquisition system can thus be optimally utilized and therefore the technical utilization of the system is maximized for patients;

the number of operating elements can be reduced thus enabling simpler and more intuitive operation;

an improved workflow and thus reduced operating times result;

support with OP documentation can be implemented by means of the functions offered.

Specifically with medical applications, there is additionally the advantage that a surgeon, who is using an image acquisition system according to the invention in the form of a video endoscopy system, only has to touch a comparatively low number of operating elements during an operation in order to utilize the complete functional scope of the endoscopy system. This is a significant advantage because the surgeon must remain sterile and thus should come into contact with the least amount of objects possible.

According to the invention, the object can also be achieved by means of further advantageous embodiments according to the dependent claims.

For example, the change in the image acquisition situation can be detected by means of a computer-implemented evaluation of the recorded image sequence. Such an evaluation, particularly by means of image analysis, can provide information, for example, as to which operating situation is specifically at hand. The evaluation of the image sequence recorded with the image sensor in this case may be based, for example, on a color analysis or may provide information regarding surgical instruments visible in the image sequence. To this end, a structural detection can be used, whereby particularly also certain organs or tissue types and, as a result, certain types of operations can be detected. In other words, the evaluation can thus assist with the identification of a specific image acquisition situation by means of characteristic structures, colors, or other information which has been obtained from the image sequence.

It is especially advantageous, in all of these situations, if the configuration takes place with the function which is needed by the user of the image acquisition system in the respectively detected image acquisition situation.

As an alternative or supplement, the detection of the change in the image acquisition situation can also take place by means of a completed actuation, for example a switch-on, of an external device and/or by means of a signal of a sensor. It is thereby possible, for example, to detect certain phases of an operation, for example a tissue resection with the assistance of an electrosurgical HF scalpel. A correspondingly suitable functionality can then be offered in response, for example smoke suppression based on image processing, which can be activated by means of one of the operating elements.

Functional reconfiguration of the operating elements can take place such that a user of the image acquisition system is adaptively offered a selection, adapted to a current image acquisition situation, of functions currently operable with the operating elements. This offer can preferably take place by means of an optic or other notification.

The operating elements may be implemented, for example, as virtual keys, particularly on a touchscreen, for example a mini-touchscreen on a camera head of an image acquisition system according to the invention in the form of an endoscopy system. In this case, the notification can take place simply in that the representation of the respective virtual key changes as soon as a new function is assigned to the virtual key and/or as soon as a functional reconfiguration of the virtual key is offered to the user.

In this case, it is desirable according to the invention when a functional scope currently operable with the operating elements is reduced as compared to a functional scope useable due to repeated reconfiguration of the operating elements. The reason for this is that specifically this function reduces the workload of the user, wherein a respective situation-dependent reconfiguration of the operating elements with functions further makes the complete functional scope accessible.

For medical applications, the invention further proposes that the operating elements are designed as mechanical manipulators and not, for example, by means of a graphical user interface (GUI). This has the advantage that the manipulators can be haptically perceived, particularly palpated, during setting of the respective function. The surgeon can thereby fully concentrate on a live video image without being distracted by the operation of a GUI.

Thus, the invention particularly proposes reassigning manual operating elements, which can be identified haptically, with functions adapted to the situation. The haptic identification capability in this case is of central significance, because it enables the surgeon to operate the operating elements blindly without having to touch nonsterile surfaces and additionally being optically distracted—as is the case with adaptive graphical user interfaces. The speed at which settings can be carried out by means of this specific embodiment is far greater than when the surgeon has to elaborately touch each newly appearing display element in a GUI, which additionally is often not even possible for reasons of sterility.

Furthermore, it is advantageous in medical applications when the operating elements are arranged on one of the components of the image acquisition system such that they can be operated and/or sterilized in a medical acquisition situation by means of individual fingers or pairs of fingers. This enables the surgeon to have simple and sterile operation of the image acquisition system. This is particularly successful when the operating elements are designed, for example, on a camera head of an endoscope of the image acquisition system.

In order to further improve the operation of the image acquisition system, the invention further proposes the display of a current functional reconfiguration of the operating elements on a display unit. This can occur preferably by means of a pictogram, which displays a spatial arrangement of the operating elements on a respective component of the image acquisition system and/or a function currently assigned to a respective one of the operating elements. The surgeon can hereby identify the current functional reconfiguration by means of a brief look at the display unit and still blindly carry out the desired settings via the operating elements and without touching the display unit. In other words, the operating elements may be separated from the display unit. Such separation may be achieved virtually or by spatially separating the operating elements from the display unit. The latter alternative is preferred in particular for cases, in which the operating elements are operated by hand. The separation may be in particular such that the current functional reconfiguration of the operating elements displayed on the display unit is a mere virtual representation of the, preferably non-virtual, operating elements. The separation thus has the advantage that when using the operating elements for setting functions of components of the image acquisition system and/or for operating these components, for example by manipulating the operating elements manually, the display unit can be used simultaneously for displaying other information such as a live video image, and this displaying may take part on parts of the display unit previously used for displaying the current functional reconfiguration of the operating elements. In other words, the display unit can be used to first visualize the user a current functional configuration of the operating elements thereby enabling the user to use the operating elements properly when viewing a live video image on the same display afterwards.

It is especially preferred in this case when the display of the current functional reconfiguration takes place parallel to a live image generated from the image sequence and displayed on the display unit. To this end, the current functional reconfiguration, particularly the mentioned pictogram, can be displayed as an overlay on the live image or in a separate window.

According to a further embodiment, a currently set and offered functional reconfiguration can then be canceled by the image acquisition system, particularly said endoscopy system, namely when a user does not acknowledge the offered functional reconfiguration. The prevents operating errors and also is less work for the surgeon.

In certain cases, using the operating elements of a component of the image acquisition system, preferably using operating elements of a camera head of an endoscope of said endoscopy system, at least one function of at least one further component of the image acquisition system/of the endoscopy system, i.e., for example, of a light source or of a camera control unit, and/or of at least one external device, for example of a surgical instrument, of a fluid pump, or an insufflator, can be set due to the complete functional reconfiguration.

In other words, a functionality of a second component of the image acquisition system/of the endoscopy system or of an external device can be operable with operating keys of a first component of the image acquisition system/of the endoscopy system due to the functional reconfiguration of the operating keys. Using this approach, the number of operating elements which must be kept sterile during an OP can be reduced, for example only the operating elements of the camera head. This is advantageous because, in this case, fewer components have to be kept sterile.

The configuration of the operating elements is preferably implemented via computer to reduce the workload on the user. Furthermore, this configuration can particularly take place continuously during recording of the image sequence and particularly such that a user of the image acquisition system, particularly of the endoscopy system, is always displayed a selection of functions assigned to the operating elements, said selection being adapted to a current recording situation, on a display unit, particularly the previously explained display unit, without the user having to carry out the configuration.

The functions which are assigned to the operating elements may relate, for example, to an adjustment of processing and/or processing of the image sequence and/or an adjustment of at least one image acquisition parameter of the image sequence such as, for example, of image brightness, image color, image contrast, or image focus. An enormous variety of functions is thereby controllable with only a few operating elements.

Additionally or alternatively in order to evaluate the image sequence, the functional reconfiguration can furthermore be carried out based on meta data from the image sequence, particularly from a video image data stream generated from the image sequence, and/or based on external data from external devices and/or on external data from sensors. These sensors may be part of the image acquisition system or installed in external devices. In any case, the image acquisition system should have, however, options enabling the scanning of sensor signals.

As previously explained, the computer-implemented evaluation of the recorded image sequence can facilitate the detection of a specific image acquisition situation. Such an image acquisition situation may be, for example, a certain phase within a medical intervention or a particular scene with characteristic image content, for example an accumulation of blood. Such an image acquisition situation normally requires a specific adjustable functional scope of the image acquisition system. Thus, in an advantageous manner, the configuration of the operating elements can specifically render this specific functional scope operable with the operating elements.

The computer-implemented evaluation of the recorded image sequence may further comprise a context-based data analysis of the image sequence. A context-based data analysis is generally understood to be analyses which support the detection of configurations in data with associated content, i.e., for example, the sequence of individual images which is recorded with the image sensor. In terms of the invention, a context-based data analysis can be understood particularly to be an evaluation of image data, particularly combined with an evaluation of meta data generated from the image sequence and/or of external data from external devices and/or from sensors, in which a certain, particularly trained, image acquisition situation, for example a certain phase of a medical intervention, is identified with computer implementation, preferably without any action on the part of the user.

According to a further aspect of the present invention, the computer-implemented evaluation, particularly said data analysis, can be supported by artificial intelligence (AI).

Said AI can be based, for example, on a neuronal network and/or on an algorithm which has been trained with the assistance of exemplary image sequences, preferably with human guidance. Such a data analysis can be used according to the invention to detect a specific, particularly predefined, image acquisition situation in order to then carry out a corresponding functional reconfiguration.

The algorithm used can thus implement artificial intelligence to detect typical image acquisition situations, for example individual phases of a surgical intervention in chronological order. In particular based on the previously implemented training, the algorithm can detect which specific image acquisition situation is present by means of characteristic properties of a current section of a video image data stream recorded with the image acquisition system. Optionally, the algorithm can subsequently select a parameter set stored for said image acquisition situation, said parameter set determining the functional reconfiguration of the operating elements.

Thus, it is especially advantageous when the algorithm has been trained using exemplary image data, by means of training monitored by a human, before use of the method on the image acquisition system. This exemplary data may be, for example, video recordings, particularly of surgical interventions. The training can consist of a surgeon dividing the video recordings into categories, wherein the algorithm is trained to detect the categories in the video recordings by means of characteristic properties of the respective video image data stream and the feedback of the surgeon.

Due to this type of artificial intelligence (AI), the algorithm is thus enabled to classify typical image acquisition situations automatically. Furthermore, the algorithm can then specify a functional reconfiguration of the operating elements which is found to be optimal for the respectively identified category, for example, by a doctor. In other words, the AI thus ensures that always the optimum functional reconfiguration of the operating elements is automatically set by the image acquisition system in any trained category of image acquisition situations, which may be typical, for example, for a certain category of surgical interventions. Optimal operation of the image acquisition system can thereby always be ensured for any detected category.

The computer-implemented evaluation of the recorded image sequence may further be based on a comparison of at least one probability indicator obtained from the image sequence with a corresponding threshold value. However, the evaluation is preferably based on a comparison of several probability indicators, which are independent of one another, each having corresponding threshold values.

Such probability indicators may be obtained, for example, by means of a parameterization of the image sequence, for example based on the detection of color, movement, structure, or pattern. Said parameterization can be provided by suitable image processing.

According to a preferred embodiment, the at least one probability indicator is obtained with the assistance of an algorithm which implements artificial intelligence (AI). Said AI may particularly be trainable or trained, particularly by means of exemplary image sequences.

With such an embodiment, it is preferable when the image acquisition system proposes a new functional reconfiguration of the operating elements only when the corresponding threshold value is exceeded. If several independent probability indicators are used, it is thus preferable when a new functional reconfiguration of the operating elements is proposed by the image acquisition system only when all of the threshold values used are exceeded. Such designs prevent overloading the surgeon with excessive proposals. A functional reconfiguration can then be suspended when the threshold values are not exceeded. Thus, the functional reconfiguration is only implemented when a change in the image acquisition situation has been detected with a preset statistical certainty, determined by at least one probability indicator.

According to the invention, in response to an actuation, for example a switch-on, of an external device such as, for example, an electrosurgical instrument, a function adapted to the external device can furthermore be assigned to one of the operating elements. Such a function may be, for example, smoke suppression based on image processing or an adaptation of image acquisition parameters. This configuration can particularly take place such that a user of the image acquisition system can activate or set the function offered via a respective operating element in order to adapt the representation of the image sequence accordingly. To this end, the image acquisition system can be in constant contact with the external device, for example via a cable or a wireless connection.

At least one of the functions which can be assigned or is assigned to one of the operating elements can facilitate the actuation of a component of the image acquisition system, particularly of the endoscopy system, or of an external device, for example a surgical instrument, a fluid pump, or an insufflator. Thus, these devices and/or components can thereby be directly controlled via the operating elements, wherein the respective operating elements may be arranged, for example, on the camera head.

With such an embodiment, it is especially advantageous when a respective operating element is assigned with a control function, for example the actuation of a flushing channel, as a function of a detected specific image acquisition situation, for example an operating scene with an accumulation of blood. The respective control function can thereby be offered on a need basis, while in cases in which the control function is not needed, for example when there is no accumulation of blood to be detected in the video image, said function is specifically not offered.

In order to achieve the aforementioned object, the features of the independent device claim are further provided according to the invention. In particular, it is thus proposed according to the invention, in order to achieve the object with an image acquisition system of the aforementioned type, that the image acquisition system comprises an image processing unit for evaluating an image sequence recorded with the image sensor as well as a control unit. In this case, the image processing unit is specifically configured to detect at least one specific image acquisition situation by evaluation of the image sequence, and the control unit is specifically configured to assign at least one function to at least one of the operating elements by means of the detected image acquisition situation.

In the case of the embodiment of the image acquisition system as an endoscopy system, it is preferred for especially simple operation when the operating elements are designed as manual operating elements on a camera head.

Furthermore, it is especially advantageous when the image acquisition system, i.e. particularly said endoscopy system, preferably said image processing unit and/or control unit, is configured to execute a method according to the invention as previously described or according to any of the claims based on an image acquisition method.

The image processing unit may be implemented locally, for example, in a camera control unit of the image acquisition system or, for example, in an external local computing unit. The image processing unit, however, may also be located off-site. Thus, the image processing unit may also be implemented, for example, by means of a local server network or by means of a cloud solution, i.e. by means of IT infrastructure which is available via the Internet.

Said operating elements may also be designed, for example, as manual operating elements, i.e., for example, by means of keys, buttons, or control dials and/or by means of virtual operating elements. Such a virtual operating element may be, for example, a virtual key which is implemented graphically on a touchscreen.

Those operating elements, to which new functions can be assigned, are designed on a camera head of an endoscope according to an especially advantageous embodiment. An especially intuitive operation of the entire endoscopy system can thereby be achieved, in which the surgeon does not have to take his/her hands off the endoscope in order to fully control the complete functional scope of the endoscopy system.

To this end, the control unit of the image acquisition system/of the endoscopy system may be configured, for example, to actuate a display unit such that the display unit displays a current functional reconfiguration of the at least one manual operating element of the camera head. As previously explained in connection with the method according to the invention, this can preferably take place by means of a pictogram. The pictogram which is displayed by the display unit can accordingly indicate particularly a spatial arrangement of the manual operating elements of the camera head and/or a function currently assigned to one of these respective operating elements.

The display of a current functional reconfiguration of the operating elements in this case enables control by the user of the image acquisition system as to specifically which current function is assigned to which operating elements.

The at least one function assigned to the at least one manual operating element may be, for example, a function of the endoscope and/or a function of a further component of the image acquisition system/of the endoscopy system, for example of a light source or of a camera control unit. Furthermore, the at least one function assigned may also be a function of at least one external device such as, for example, a surgical instrument.

The result of this is that a plurality of functions of the image acquisition system/of the endoscopy system, i.e., for example not only functions of the endoscope itself but also of other components of the image acquisition system/of the endoscopy system or, however, of external devices, can be controllable via the operating elements, preferably via manual operating elements of a camera head of the image acquisition system.

With such embodiments, the camera head can thus take on the role of a central control element to the extent that the user does not have to take the hand off of the camera head in order to operate these components and/or devices, whereby working with the endoscopy system is greatly simplified. In particular, as previously explained, only the operating elements on the camera head must be kept sterile but no longer other operating elements on other components, because they are rendered superfluous by the invention.

It is especially advantageous for simplified operation of the image acquisition system accordingly when the at least one function facilitates the control and/or adjustment of a component of the image acquisition system and/or of an external device.

Furthermore, the at least one function may also relate to an adjustment of processing and/or processing of the image sequence and/or setting of at least one image acquisition parameter of the image sequence, for example image brightness, image color, image contrast, or image focus. It is hereby significant that an enormous spectrum of functions with only very few manual operating elements is hereby provided by means of the invention.

Of course, further manual operating elements may be designed on the endoscope and/or on a light source and/or on a camera control unit, of the respective image acquisition system and/or of the endoscopy system. In this case, it is advantageous when the control unit is specifically configured to assign at least one further function to at least one of these further manual operating elements as a function of a detected image acquisition situation. The basic idea of the invention can hereby be expanded to other components of the image acquisition system/of the endoscopy system starting from the camera head.

The respective function in this case may preferably be specifically a function of those components, the further manual operating element of which is assigned by the control unit. If a further operating element is designed, for example, on the light source, it makes sense if the control unit assigns a function of the light source to the operating element of the light source as a function of a detected image acquisition situation.

It is presumed that the image acquisition system/the endoscopy system has a number of functions stored as assignable. According to the invention, it is then suitable, in order to achieve intuitive operation, when a number of functions exceeds a number of the operating elements, to which the control unit can assign the stored functions, by at least the factor of 2, preferably however by at least the factor of 5. This design rule thus gives an instruction as to how many operating elements appear to be necessary for intuitive operation starting from a predefined desired functional scope of the image acquisition system/of the endoscopy system.

The invention is described in greater detail below by means of exemplary embodiments but is not limited to these exemplary embodiments. Further embodiments of the invention can be obtained from the following description of a preferred exemplary embodiment in conjunction with the general description, the claims, as well as the figures.

With the following description of various preferred embodiments of the invention, elements corresponding in function are also given corresponding reference numerals, even when there is a deviating design or shape.

BRIEF DESCRIPTION OF THE DRAWINGS

The following is shown.

DETAILED DESCRIPTION

Figure 1:
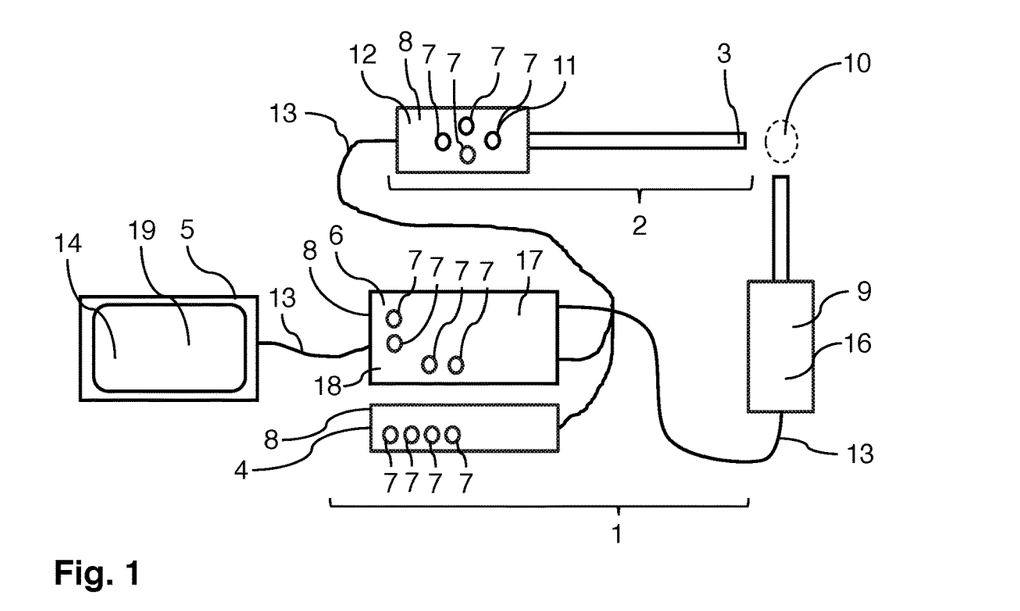
FIG. 1 a schematic view of an image acquisition system according to the invention in the form of an endoscopy system.

FIG. 1 shows an image acquisition system 1 according to the invention in the form of an endoscopy system which comprises several components 8, namely: An endoscope 2 with a camera head 12, which reads out an image sensor 3 of the endoscope 2 and on which operating elements 7 are formed in the form of several keys and rotary knobs, i.e. mechanical manipulators 11; a corresponding camera control unit 6 for processing an image sequence recorded with the image sensor 3 in the form of a video image data stream; as well as a light source 4 for illuminating a region of interest (ROI), i.e. the particular object region which is of interest and being examined with the endoscope 2, as is illustrated in FIG. 1. To this end, the light source 4 is connected to the endoscope 2 by means of fiber optics.

As can further be seen in FIG. 1, the endoscopy system 1 is connected to a display unit 5, in the form of an external monitor, via a cable and connected to an external device 9, in the form of a surgical instrument 16, via a further cable 13. The video image data stream is displayed as a live video image 19 on the display unit 5.

Furthermore, the components 8 of the endoscopy system 1 are connected to one another by means of several cables 13, via which control signals can be exchanged. Thus, the endoscope 2, for example, can access the light source 4 via the camera control unit 6 and vice versa. In addition, the camera control unit 6 can transmit image and control signals to the display unit 5 as well as detect signals transmitted from the surgical instrument 16.

When the endoscopy system 1 is placed in operation, the operating elements 7 are initially on the camera head 12 in a default setting, assigned with respective default functions. These default functions enable the setting/operation of functions of the endoscope 2 with the keys and control dials on the camera head 12, namely the readjustment, inter alia, of a zoom factor and the setting of image brightness, i.e. the setting of image acquisition parameters.

The endoscopy system 1, or more precisely the camera control unit 6, further comprises an image processing unit 17 for evaluating the image sequence recorded with the image sensor 3 as well as a control unit 18.

The image processing unit 17 is configured to detect at least one specific image acquisition situation by means of evaluation of the image sequence. Thus, if the image acquisition situation depicted by the image sequence changes from a first to a second image acquisition situation, this change can be detected by the image processing unit 17.

For example, the image processing unit 17 is capable of detecting the development of smoke in the region of interest 10 by means of a computer-implemented evaluation of the recorded image sequence. If the specific image acquisition situation "Smoke in image" is detected by the image processing unit 17, the control unit 18 assigns a new function to one of the operating elements 7 on the camera head 12.

This function consists of the activation or deactivation (by pressing the key again) of an image processing algorithm, which suppresses the smoke in the image sequence. As a result, the user of the endoscope can thus immediately activate said smoke suppression function by actuating the particular operating element 7, the function of which has been reassigned by the control unit 18 of the endoscopy system 1, in response to the change in the image acquisition situation detected by the image processing unit 17, as soon as smoke can be seen in the live video image 19.

Figure 3:
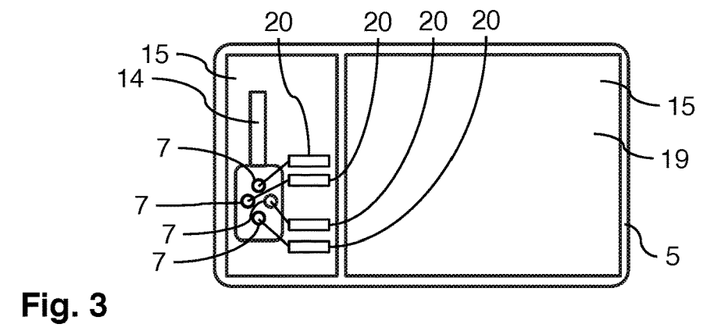
FIG. 3 an illustration of a display unit of the endoscopy system from FIG. 1 in a particular display situation.

In order to inform the user which of the operating elements 7 embodied on the camera head 12 has been assigned with the new function, a pictogram 14 is displayed on the display unit 5, as illustrated in FIG. 3, in a separate window 15, in addition to the live video image 19, in which said pictogram indicates a schematic representation of the endoscope 2 including the camera head 12 and particularly the spatial arrangement of the operating elements 7 on the camera head 12, as a comparison of the operating elements 7, illustrated as circles, shows in FIGS. 3 and 1.

The user in this case is displayed which function is currently assigned to which operating element 7 by the endoscopy system 1 by means of several displayable display elements 20. Using this approach, the user is adaptively and visually shown, namely in response to the changed image acquisition situation, a selection of functions currently controllable with the operating elements 7, said selection being adapted to the current "Smoke in image" image acquisition situation, namely by means of the optical notifications which are generated by the displayable display elements 20.

Because one of the four keys on the camera head 12 has been configured with the smoke suppression function by the control unit 18, the default function, which was adjustable in the default setting with said key, can initially no longer be operated. In other words, the functional scope respectively controllable currently with the operating keys is accordingly smaller, as an entire functional scope, which is usable by means of repeated functional reconfigurations of the operating elements 7. Thus, the endoscopy system 1 offers the user only a reduced functional scope respectively adapted to the situation. This reduces the workload on the user and thus simplifies operation. At the same time however, the complete functional scope can continue to be utilized.

As an alternative to the detection of the "Smoke in image" image acquisition situation by the image processing unit 17, a change in the image acquisition situation can also be detected by the endoscopy system 1 by means of a signal of the surgical instrument 16. When the surgical instrument 16, which is an HF scalpel, is switched on, this switch-on is detected by the camera control unit 6 via the cable 13. Because it is expected in this case that smoke will develop in the near future, namely when tissue is resected with the HF scalpel, the control unit 18 preventively implements the reconfiguration of one of the operating elements 7 with the smoke suppression function in response to the change in the image acquisition situation detected by means of the signal of the surgical instrument 16.

At the same time, the user is displayed the reconfiguration of the functional key by means of the pictogram 14 to the extent that the user can switch on the smoke suppression function before the smoke develops. To do this however, the user must first acknowledge, by means of one of the operating elements 7, the functional reconfiguration offered via the pictogram 14.

If the user does not do this within a predefined time interval, the endoscopy system 1 cancels the offered functional reconfiguration to the extent that the smoke suppression function is no longer operable with the operating element 7 but instead the function previously assigned to the operating element 7 in question. Accordingly, the display of the pictogram 14 is also updated after cancellation of the functional reconfiguration. Thus, the user remains in control of the functions currently controllable via the operating elements 7, despite the functional reconfiguration.

By means of the signal of the surgical instrument 16, the control unit 18, however, not only assigns the smoke suppression function to one of the operating elements 7 but additionally assigns a function for controlling the surgical instrument 16, namely regulation of the electrical output of the HF scalpel, to another one of the operating elements 7 of the camera head 12. Due to this additional functional reconfiguration with this further operating element 7 of the camera head 12, the output of the surgical instrument 16 can thereby be adjusted.

Furthermore, the control unit 18 assigns, in turn, the new function "Control image contrast" to another one of the operating elements 7 on the camera head 12, with said new function, the image acquisition parameter known as image contrast can be adjusted by means of processing the recorded image sequence. This functional reconfiguration is also immediately displayed automatically in the pictogram 14 with the assistance of a display element 20.

As a result, the user is thus displayed, on the display unit 5, a selection, adapted to the "Smoke in image" situation, of three new functions assigned to the operating elements 7. Thus, the user has a functional scope, controllable by means of the operating elements 7, which can be considered optimum for the detected "Smoke in image" image acquisition situation. The reason for this is the user can switch on the smoke suppression, control the output of the HF scalpel, and simultaneously adapt the image contrast immediately, without the user himself/herself having to carry out said functional reconfiguration of the operating elements 7 by means of tedious adjustments.

Instead, a simple acknowledgment with one of the operating elements 7 is sufficient for this without complex searching through submenus as with conventional endoscopy systems. Thus, the operation of the endoscopy system 1 is decisively improved. The reason for this is that specifically the particular functional scope of the endoscopy system 1 which is required/suitable in the detected image acquisition situation is controllable via the operating elements 7 due to the automatic functional reconfiguration.

The configuration of the operating elements 7 takes place continuously and implemented via computer during operation of the endoscopy system 1 by means of the control unit 18, because the image processing unit 17 continuously analyzes the video image data stream for changes in the image acquisition situation.

As previously mentioned, the detection of the change in the image acquisition situation by means of recognition of a specific image acquisition situation is based on a computer-implemented evaluation of the recorded image sequence by means of the image processing unit 17. To this end, said image processing unit uses an algorithm which has been trained, under human guidance, with the assistance of exemplary image sequences. The image processing unit 17 is thereby rendered capable of detecting a number of predefined image acquisition situations by means of predefined parameters, which have been trained respectively previously by means of the exemplary image sequences. Thus, artificial intelligence for determining certain image acquisition situations is implemented based on the algorithm.

More precisely, the algorithm calculates image parameters from the image sequence and obtains several probability indicators therefrom, which the algorithm respectively compares with corresponding threshold values. If all threshold values are exceeded, this is evaluated such that the image acquisition situation, which is characterized by the image parameters and threshold values, has been detected with a certain statistical minimum certainty.

For example, by means of a calculated color value and a corresponding calculated image portion of pixels of said color value, the image processing unit 17 detects whether the image sequence is currently showing a greater accumulation of blood by means of a comparison with corresponding threshold values. As a function of the thereby detected "Accumulation of blood in image" image acquisition situation, the control unit 18 then assigns a function known as "Switch flushing channel on/off" to one of the operating elements 7 to the extent that, with said operating element 7, an external rinse water pump can be actuated, with which the accumulation of blood in the region of interest 10 being examined with the endoscope 2 can be eliminated.

In contrast, if one of the threshold values is not met, this functional reconfiguration is suppressed. Faulty image detections can thereby be reduced to the extent that the user is not repeatedly disturbed when working by unnecessary functional reconfigurations.

The fact that the manual operating elements 7 on the camera head 12 are designed as mechanical manipulators 11 in the form of rotary knobs and keys has the decisive advantage that the user can haptically perceive the operating elements 7 when said user operates the function linked to the respective operating element 7. Thus, the user can fully concentrate on observing the live video image 19, because the user can blindly operate the operating elements 7. Furthermore, the operating elements 7 are specifically arranged such that they are operable in the medical recording situation shown in FIG. 1 by means of individual fingers. This all means that the user specifically does not have to touch the display unit 5 in order to carry out adjustments of the functions there such that sterility can be ensured.

Figure 4:
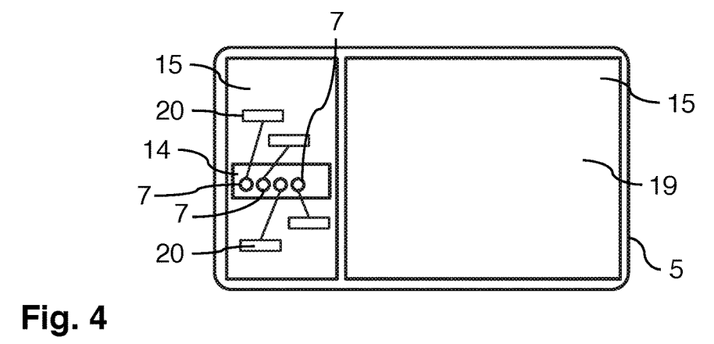
FIG. 4 a further display situation of the display unit from FIG. 3.

As shown in FIG. 4, the endoscopy system 1 can also reassign operating elements 7 on other components 8 with functions, for example the operating elements 7 of the light source 4, in response to the detection of certain recording situations, which can also be seen in FIG. 1 and in the pictogram 14 of the light source 4 in the left-hand window 15 of the FIG. 4. Here as well, the functional reconfiguration is again shown to the user initially with the assistance of the pictogram 14 and optical notifications by means of display elements 20 on the display unit 5, and the user must acknowledge said offered functional reconfiguration so that it is also actually implemented by the endoscopy system 1.

Figure 5:
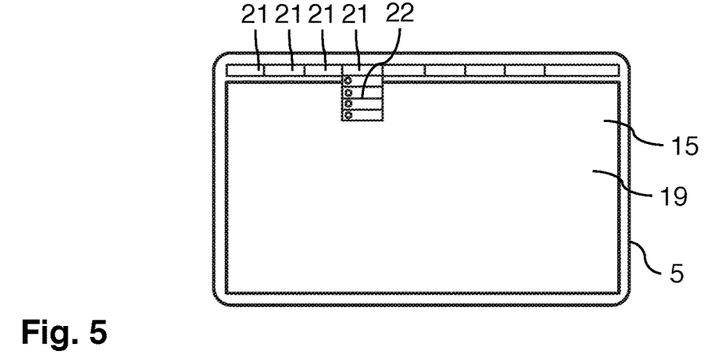
FIG. 5 yet another display situation of the display unit from FIG. 3.

Depending on the detected image acquisition situation, the left-hand window can also be hidden, as illustrated in FIG. 5, to the extent that almost the entire monitor is taken up by the live video image 19. In this case, the current functional reconfiguration can be displayed, as shown in FIG. 5, by means of respective drop-down menus 22, wherein each of the tabs 21 shown in FIG. 5 indicate the functional configuration of the operating elements of a component 8 of the endoscopy system 1.

Figure 6:
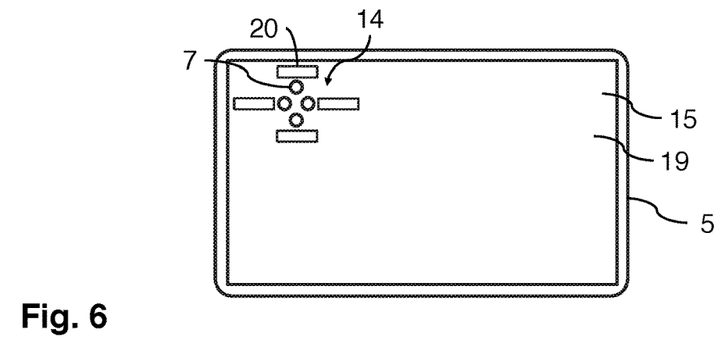
FIG. 6 a fourth display situation of the display unit from FIG. 3.

FIG. 6 shows another option for displaying the current functional reconfiguration or for visually offering a functional reconfiguration yet to be acknowledged. In this case, the pictogram 14 is limited to the spatial arrangement of the operating elements 7 and is displayed in the same window 15 as an overlay over the live video image. Here as well, the respective current or offered new function of the respective operating element 7 is displayed to the user by means of displayed display elements 20.

Figure 2:
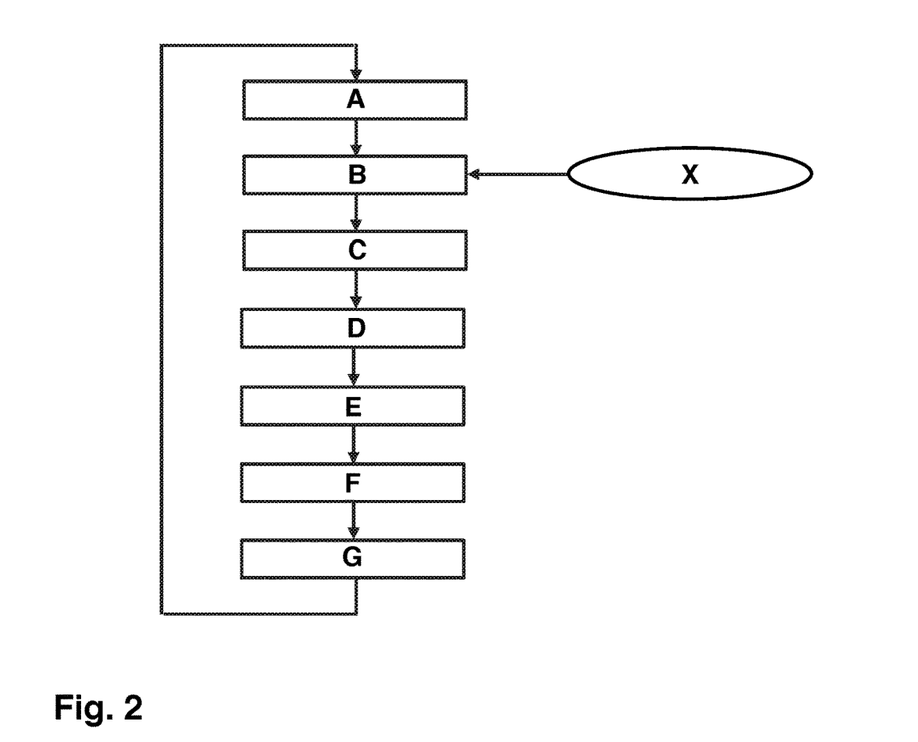
FIG. 2 a signal flowchart in order to explain a method according to the invention.

Finally, FIG. 2 shows, by means of the signal flowchart shown, practical implementation of a method according to the invention based on the following method steps:

A. recording the image sequence with the endoscopy system in the form of a video image data stream;
B. computer-implemented evaluating of the recorded image sequence with the assistance of the image processing unit 17;
C. calculating image parameters and probability indicators using the evaluation;
D. comparing the probability indicators with threshold values (optional step);
E. generating a recommendation for a functional reconfiguration of at least one of the operating elements 7; (this step does not take place if there has been no change detected in the image acquisition situation or the change was detected with insufficient certainty, which is determined by means of the threshold value comparison);
F. offering a recommendation (visually, e.g. with the assistance of a pictogram 14, or acoustically).
G. The user acknowledges the visual recommendation by accepting, rejecting, or doing nothing (which is evaluated as rejecting)—this can occur through speech commands, gestures, or by means of the operating elements 7; if the user accepts, the recommendation is implemented, i.e. the new function is assigned to the operating element 7.

Finally, optional step X shown in FIG. 2 comprises the use of artificial intelligence during the computer-implemented evaluation of the recorded image sequence.

In summary, to simplify operation of a medical image acquisition system 1, it is proposed that the image acquisition system 1 continuously monitors a current image acquisition situation and assigns at least one new function to at least one, preferably manual, operating element 7, which is adapted to a detected new image acquisition situation, in response to a change in the image acquisition situation, to the extent that said newly assigned function is operable and/or adjustable with the at least one operating element 7. To this end, the image acquisition system 1 can detect the change in the image acquisition situation using predefined parameters by means of sensors and/or through communication with peripheral units and/or preferably through image analysis of an image sequence which is recorded with an image sensor 3 of the image acquisition system 1 (cf. FIG. 1).

What is claimed is:

1. An image acquisition method, wherein an image sequence is recorded with an image sensor of a medical image acquisition system and wherein, with the assistance of operating elements, functions of components of the image acquisition system are set and/or operated, wherein at least one function is newly assigned to at least one of the operating elements in response to a detected change in an image acquisition situation such that the at least one operating element is automatically reassigned with a new function, not previously being controllable with the at least one operating element before the assignment, and a user can adjust and/or operate said new function by manually operating said at least one of the operating elements;
wherein the change in the image acquisition situation is detected by an image processing unit of the image acquisition system as a specific image acquisition situation based on a comparison of a probability indicator obtained from the image sequence with a corresponding threshold value.

2. The image acquisition method according to claim 1, wherein the detection of the change in the image acquisition situation occurs by means of a computer-implemented evaluation of the recorded image sequence and/or by means of a completed actuation, for example a switch-on, of an external device and/or by means of a signal of a sensor.

3. The image acquisition method according to claim 1, wherein a previously implemented user input is considered during the reassignment, such that the reassignment corresponds to an individual preference of a user of the image acquisition system.

4. The image acquisition method according to claim 1, wherein the functional reassignment or functional reconfiguration takes place such that a user of the image acquisition system is adaptively offered a selection, adapted to a current image acquisition situation, of functions currently operable with the operating elements, by means of an optical or other notification, wherein a functional scope currently operable with the operating elements is reduced as compared to a functional scope useable due to repeated reconfiguration of the operating elements.

5. The image acquisition method according to claim 1, wherein the operating elements are designed as mechanical manipulators, which are haptically perceived during setting of the respective function, and/or wherein the operating elements are arranged on one of the components, such that they can be operated and/or sterilized in a medical acquisition situation by means of individual fingers or pairs of fingers.

6. The image acquisition method according to claim 1, wherein a current functional reconfiguration of the operating elements is displayed on a display unit, such that the current functional reconfiguration displayed on the display unit is a mere virtual representation of the operating elements and/or such that when using the operating elements for setting functions of components of the image acquisition system and/or for operating these components, the display unit can be used simultaneously for displaying other information such as a live video image on parts of the display unit previously used for displaying the current functional reconfiguration of the operating elements.

7. The image acquisition method according to claim 6, wherein the current functional reconfiguration of the operating elements is displayed on the display unit by means of a pictogram, which displays a spatial arrangement of the operating elements on a respective component of the image acquisition system and/or a function currently assigned to a respective one of the operating elements, and/or wherein a currently set and offered functional reconfiguration is again canceled by the image acquisition system if a user does not acknowledge the offered functional reconfiguration.

8. The image acquisition method according to claim 1, wherein at least one function of at least one further component of the image acquisition system/of the endoscopy system is set, for example of a light source or of a camera control unit, and/or of at least one external device, for example of a surgical instrument, of a fluid pump/an insufflator, due to the functional reconfiguration with the operating elements of a component of the image acquisition system.

9. The image acquisition method according to claim 1, wherein the configuration of the operating elements is computer-implemented and/or takes place continuously during a recording of the image sequence, such that a user of the image acquisition system is always displayed, on a display unit, a selection of functions assigned to the operating elements, said selection being based on a current recording situation, without the user having to carry out the configuration.

10. The image acquisition method according to claim 1, wherein a function assigned to the operating elements relates to an adjustment of processing and/or processing of the image sequence and/or setting of at least one image acquisition parameter of the image sequence, for example image brightness, image color, image contrast, or image focus.

11. The image acquisition method according to claim 1, wherein, additionally or alternatively in order to evaluate the image sequence, the functional reconfiguration is carried out based on meta data from the image sequence, and/or based on external data from external devices and/or from sensors.

12. The image acquisition method according to claim 1, wherein the computer-implemented evaluation of the recorded image sequence facilitates the detection of a specific image acquisition situation, or a certain scene with characteristic image content, which requires a specific adjustable functional scope of the image acquisition system, wherein the assignment of the operating elements renders this specific functional scope operable with the operating elements.

13. The image acquisition method according to claim 1, wherein the computer-implemented evaluation of the recorded image sequence comprises a context-based data analysis of the image sequence, which is supported by artificial intelligence, based on a neuronal network and/or on an algorithm which has been trained with the assistance of exemplary image sequences, and/or which facilitates the determination of a certain image acquisition situation.

14. The image acquisition method according to claim 1, wherein computer-implemented evaluation of the recorded image sequence is based on a comparison of at least one probability indicator obtained from the image sequence with a corresponding threshold value, wherein the image acquisition system proposes a new functional reconfiguration of the operating elements only when the corresponding threshold value is exceeded; wherein the at least one probability indicator is obtained with the assistance of an algorithm which implements artificial intelligence.

15. The image acquisition method according to claim 1, wherein, in response to an actuation of an external device, a function adapted to the external device, for example smoke suppression based on image processing or an adaptation of image acquisition parameters, is assigned to one of the operating elements, such that a user of the image acquisition system can activate or set the function offered via the respective operating element in order to adapt the representation of the image sequence accordingly wherein, to this end, the image acquisition system is in constant contact with the external device.

16. The image acquisition method according to claim 1, wherein at least one of the functions which can be assigned or is assigned to one of the operating elements facilitates the actuation of a component of the image acquisition system or of an external device, a surgical instrument, a fluid pump, or an insufflator, wherein a respective operating element is assigned with a control function as a function of a detected specific image acquisition situation.

17. A medical image acquisition system comprising an image sensor as well as several operating elements for controlling the image acquisition system, wherein the image acquisition system comprises an image processing unit for evaluating an image sequence recorded with the image sensor as well as a control unit, wherein the image processing unit is specifically configured to detect at least one specific image acquisition situation by evaluation of the image sequence, and the control unit is specifically configured to assign at least one function to at least one of the operating elements by means of the detected image acquisition situation; and wherein the at least one operating element is automatically reassigned with a new function, not previously being controllable with the at least one operating element before the assignment, and a user can adjust and/or operate the new function by manually operating the at least one of the operating elements;

wherein the image acquisition situation is detected by the image processing unit based on a comparison of a probability indicator obtained from the image sequence with a corresponding threshold value.

18. The image acquisition system according to claim 17, wherein the image processing unit is implemented in a camera control unit of the image acquisition system or in an external local computing unit or by means of a local server network or by means of IT infrastructure which is available via the Internet (cloud).

19. The image acquisition system according to claim 17, wherein those operating elements, to which new functions can be assigned, are designed on a camera head of the image acquisition system, and/or wherein the control unit is specifically configured to actuate a display unit such that the display unit displays a current functional reconfiguration of the at least one manual operating element of the camera head, which displays a spatial arrangement of the manual operating elements of the camera head and/or a function currently assigned to one of these respective operating elements.

20. The image acquisition system according to any of claim 17, wherein the at least one function assigned to the at least one manual operating element is a function of an endoscope/exoscope/microscope and/or a function of a further component of the image acquisition system.

21. The image acquisition system according to claim 17, wherein the at least one function facilitates the control and/or adjustment of a component of the image acquisition system, and/or of an external device and/or relates to an adjustment of processing and/or processing of the image sequence and/or setting of at least one image acquisition parameter of the image sequence.

22. The image acquisition system according to claim 17, wherein further manual operating elements are designed on the endoscope/exoscope/microscope and/or on a light source and/or on a camera control unit of the respective image acquisition system, and the control unit is specifically configured to assign at least one further function to at least one of these further manual operating elements, as a function of a detected image acquisition situation, preferably wherein the respective function is a function of those components, the further manual operating element of which is assigned by the control unit.

23. The image acquisition system according to claim 17, wherein a number of functions stored as assignable exceeds a number of the operating elements, to which the control unit can assign the stored functions, by at least the factor of 2.

\* \* \* \* \*